United States Patent [19]

Hofmann et al.

[11] 4,216,148

[45] Aug. 5, 1980

[54] 4H-THIENO[3,4-B][1,4]BENZODIAZEPINES

[75] Inventors: Corris M. Hofmann, Ho-Ho-Kus, N.J.; Jeffery B. Press, Bellvale, N.Y.; Sidney R. Safir, River Edge, N.J.

[73] Assignee: American Cyanamid Company, Stamford, Conn.

[21] Appl. No.: 7,853

[22] Filed: Jan. 30, 1979

[51] Int. Cl.³ .................. C07D 495/04; A61K 31/495
[52] U.S. Cl. .................................. 260/243.3; 424/250
[58] Field of Search ...................................... 260/243.3

[56] References Cited

U.S. PATENT DOCUMENTS

| 3,951,981 | 4/1976 | Safir | 260/243.3 |
| 4,087,421 | 5/1978 | Safir | 260/243.3 |

*Primary Examiner*—Jose Tovar
*Attorney, Agent, or Firm*—Edward A. Conroy, Jr.

[57] ABSTRACT

This disclosure describes substituted 9-(4-methyl-1-piperazinyl)-4H-thieno[3,4-b][1,4]benzodiazepines which possess analgesic and anti-depressant activity and are also useful as anti-psychotic or neuroleptic agents.

7 Claims, No Drawings

4H-THIENO[3,4-B][1,4]BENZODIAZEPINES

BRIEF SUMMARY OF THE INVENTION

This invention relates to new organic compounds and, more particularly, is concerned with novel substituted 9-(4-methyl-1-piperazinyl)-4H-thieno[3,4-b][1,4]benzodiazepines which may be represented by the following structural formula:

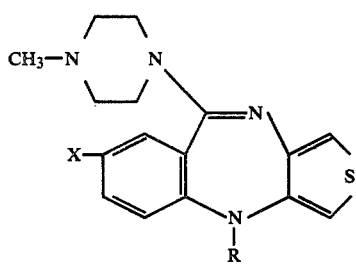

wherein R is hydrogen or methyl and X is hydrogen, fluoro for chloro.

DETAILED DESCRIPTION OF THE INVENTION

The novel compounds of the present invention are obtainable as crystalline materials having characteristic melting points and absorption spectra. They are appreciably soluble in many organic solvents such as lower alkanols, acetone, ethyl acetate, and the like but are generally insoluble in water. These compounds are organic bases and thus are capable of forming acid-addition salts with a variety of organic and inorganic salt-forming reagents. Thus, acid-addition salts, formed by admixture of the organic free base with an equivalent of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the novel compounds of the present invention are, in general, crystalline solids relatively soluble in water, methanol and ethanol but relatively insoluble in non-polar organic solvents such as diethyl ether, benzene, toluene, and the like. For purposes of this invention, the free bases are equivalent to their non-toxic acid-addition salts.

The compounds of the present invention are physiologically active on the central nervous system. They show high activity as anti-psychotic or neuroleptic agents, as antidepressants and as analgesics.

A useful test for anti-psychotic acitvity consists of measuring the reduction of spontaneous motor activity in animals. This test has been described by W. D. Gray, A. C. Osterberg and C. E. Rauh, Arch. Int. de Pharmaco. et de Therapie, 134, 198–215, (1961) and by W. J. Kinnard and C. J. Carr, J. Pharmaco. and Exp. Ther., 121, 354–361, (1957). The test compounds are administered orally to six to ten individual rats in graded doses. After one hour, a five minute count of motor activity is recorded in an activity counter (Animex ®, Farad Electronics, Sweden). A compound is considered active at a given dose if it causes a 50% reduction of the motor activity count when compared to controls. The results for typical compounds of this invention are given in Table I.

Table I

| Compound | Result |
|---|---|
| 4-Methyl-9-(4-methyl-1-piperazinyl)-4H-thieno[3,4-b] [1,4]benzodiazepine fumarate | Active |
| 9-(4-Methyl-1-piperazinyl)-4H-thieno-[3,4-b] [1,4]benzodiazepine fumarate | Active |

In a second test for anti-psychotic activity, the compounds of this invention were measured for their ability to protect grouped mice from the lethal effect of d-amphetamine. Known anti-psychotics such as chlorpromazine and haloperidol protect grouped mice from the lethal effects of d-amphetamine sulfate, wheras other types of "tranquilizers" such as chlordiazepoxide and diazepam are ineffective. Groups of 10 mice are treated orally with the test compounds at a dose of 5 or 10 mg./kg. of body weight. After periodic absorption times the mice are subsequently given intraperitoneal injections of d-amphetamine sulfate at a dose of 15 mg./kg. of body weight. The time of peak effect is established as the absorption time for the respective compounds that protect the greatest percentage of mice from death within 24 hours, with equal to or greater than 50% protection being considered active. The results for typical compounds of this invention appear in Table II.

Table II

| Compound | Result |
|---|---|
| 4-Methyl-9-(4-methyl-1-piperazinyl)-4H-thieno[3,4-b] [1,4]benzodiazepine fumarate | Active |
| 9-(4-Methyl-1-piperazinyl)-4H-thieno-[3,4-b] [1,4]benzodiazepine fumarate | Active |
| 7-Chloro-9-(4-methyl-1-piperazinyl)-4H-thieno[3,4-b] [1,4]benzodiazepine | Active |
| 7-Fluoro-9-(4-methyl-1-piperazinyl)-4H-thieno[3,4-b] [1,4]benzodiazepine | Active |
| 7-Fluoro-4-methyl-9-(4-methyl-1-piperazinyl)-4H-thieno[3,4-b] [1,4]benzodiazepine hemifumarate | Active |

In a third test, the anti-depressant activity of the compounds is measured by their ability to inhibit tetrabenazine induced depression of exploratory behavior in mice. Varying doses of the test compounds are administered intraperitoneally or orally to 5 mice, one hour before the administration of tetrabenazine hexamate at an intraperitoneal dose of 30 mg./kg. of body weight, which dose is known to depress markedly the exploratory behavior of normal mice. Thirty minutes later the mice are tested for their exploratory behavior by placing individual mice in the center of a horizontal disc. Inhibition of the depression induced by tetrabenazine is considered present if the mice perform one or more of the following actions within 10 seconds after being placed on the disc:

1. Mice move to the edge of the disc and peer over the side.
2. Mice move 180° in place.
3. Mice display a head movement of 90° immediately followed by a head movement in the opposite direction of at least 45°.

Administration of the test compounds to additional groups of 5 mice is repeated, the numbers of individual mice showing an anti-depressant response (normal exploratory behavior) is recorded and the results are analyzed by the following scheme (statistically standardized; significant P=less than 0.05).

|  | No. Active/No. Tested | Result |
|---|---|---|
| First stage | 0/5 | Reject (ineffective anti-depressant) |
|  | 1/5–3/5 | Continue to second stage |
|  | ≧4/5 | Accept (active anti-depressant) |
| Second stage | 1/10 | Reject |
|  | 2/10–3/10 | Continue to third stage |
|  | ≧4/10 | Accept |
| Third stage | <4/15 | Reject |
|  | ≧4/15 | Accept |

When a given compound is accepted by this procedure at the designated dose level, the sequential procedure is repeated at the same dose level to provide unequivocal confirmation of its acceptance as an active anti-depressant. This method has been described by E. N. Greenblatt and A. C. Osterberg, Toxicology and Applied Pharmacology, 7, 566–578 (1965). The results for typical compounds of this invention appear in Table III.

| Compound | Result |
|---|---|
| 7-Chloro-4-methyl-9-(4-methyl-1-piperazinyl)-4H-thieno[3,4-b] [1,4]benzodiazepine fumarate | Active |
| 7-Fluoro-4-methyl-9-(4-methyl-1-piperazinyl)-4H-thieno[3,4-b] [1,4]benzodiazepine hemifumarate | Active |

In order to demonstrate analgesic activity, a test is used [(D. C. Atkinson and A. Cowan, J. Pharm. Pharmacol., 26, 727 (1974)] in which male, albino, Wistar strain rats from Royalhart farms, weighing 120–150 g. are deprived of food for about 20 hours. A 40% suspension of brewers' yeast in physiological saline is injected, at a dose of 0.25 ml./rat, into the plantar surface of the left hind paw. Three hours later, at which time an inflammation of the injected paw has developed, a pre-drug assessment of walking gait is made for each rat according to the following scoring system:

0 = Normal gait in the presence of a severely inflamed paw. There is continuous use of the foot pad.
0.5 = As above with intermittent mild limping.
1.0 = Continuous limping, but continuous use of the foot pad.
1.5 = Limping with occasional three-legged gait (paw kept off walking surface) or intermittent use of digits in combination with foot pad.
2.0 = Continuous three-legged gait and/or only the tips of the digits touch the walking surface. There is no use of the foot pad.

More than 95% of the rats exhibit a gait score of 2.0 before being given a test compound. Test compounds, in a suitable vehicle, are administered orally by gavage in a volume of 0.5 ml./100 g. of body weight. One and/or two hours later a post-drug assessment of walking gait is made. The post-treatment score is then measured and compared with the pretreatment score. A compound is considered active when there is ≧50% reversal of the abnormal gait score (≦1.0 post-drug) from the pre-drug score (2.0). The results for typical compounds of this invention appear in Table IV.

| Compound | Result |
|---|---|
| 9-(4-Methyl-1-piperazinyl)-4H-thieno[3,4-b] [1,4]benzodiazepine fumarate | Active |
| 7-Chloro-9-(4-methyl-1-piperazinyl)-4H-thieno[3,4-b] [1,4]benzodiazepine | Active |

The active components of this invention can be used in compositions such as tablets, the principal active ingredient being mixed with conventional tableting ingredients such as corn starch, lactose, sucrose, sorbitol, talc, stearic acid, magnesium stearate, dicalcium phosphate, gums or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The liquid forms in which the novel compositions of the present invention may be incorporated for administration include suitably flavored emulsions with edible oils, such as cottonseed oil, sesame oil, coconut oil, peanut oil, and the like, as well as sterile suspensions for parenteral use.

The term dosage form as described herein refers to physically discrete units suitable as unitary dosage for a warm-blooded animal subject, each unit containing a predetermined quantity of active component calculated to produce the desired therapeutic effect in association with the required pharmaceutical diluent carrier or vehicle. The dosage may vary from one to 70 mg./kg. of warm-blooded animal per day, preferably in multiple doses. The daily dosage requirement may be from 50 to 2000 mg. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The invention will be described in greater detail in conjunction with the following specific examples.

EXAMPLE 1

4-Methyl-9-(4-methyl-1-piperazinyl)-4H-thieno[3,4-b][1,4]benzodiazepine fumarate A mixture of 160 g. of methyl tetrahydro-4-oxo-3-thiophenecarboxylate [R. B. Woodward et al., J. Am. Chem. Soc., 68, 2232 (1946); O. Hromatka et al., Monatsh. Chem., 104, 1520 (1973)] and 1.0 g. of p-toluenesulfonic acid is refluxed overnight in isopropenyl acetate. Excess solvent is removed through a Vigreux column and the residue is distilled in vacuo bp. 94–96° C. to give 179.5 g. of 2,5-dihydro-4-hydroxy-3-thiophenecarboxylic acid, methyl ester, acetate.

The product above (179.5 g.) in 375 ml. of methylene chloride is cooled to −25° C. and treated with 80 ml. of sulfuryl chloride which is added dropwise over a period of one hour to maintain −25° C. The mixture is stirred an additional 0.5 hour at −25° C., then is allowed to stir at room temperature overnight. Excess reagent and solvent are removed through a Vigreux column and the residue is distilled in vacuo bp. 104–106° C. to yield 158.2 g. of 4-hydroxy-3-thiophenecarboxylic acid, methyl ester, acetate.

A 50.0 g. portion of the preceding product and 4.0 ml. of concentrated sulfuric acid in 750 ml. of ethanol is refluxed for 72 hours. The mixture is concentrated to a volume of 200 ml. and diluted with 200 ml. of water. The aqueous solution is extracted with five 200 ml. portions of ether. The combined organic layer is washed with three 250 ml. portions of 1 N sodium hydroxide, then is dried with brine and anhydrous sodium sulfate. Concentration and distillation in vacuo bp. 92°–98° C. yields 38.9 g. of 4-ethoxy-3-thiophenecarboxylic acid, ethyl ester as a pale yellow liquid.

An 8.0 g. portion of 4-ethoxy-3-thiophenecarboxylic acid, ethyl ester and 5.0 ml. of hydrazine hydrate in 25 ml. of ethanol is refluxed overnight. The reaction mixture is quenched with 50 ml. of water, then is extracted with five 100 ml. portions of methylene chloride. The combined organic extracts are dried over anhydrous sodium sulfate and evaporated to yield 7.20 g. of 4-ethoxy-3-thiophenecarboxylic acid hydrazide as a white solid.

A 7.42 g. amount of 4-ethoxy-3-thiophenecarboxylic acid hydrazide is dissolved in 100 ml. of 3 N hydrochloric acid and 150 ml. of glacial acetic acid, 150 ml. of chloroform is added and the mixture is cooled to 5° C. then a solution of 2.79 g. of sodium nitrite in 25 ml. of water is added dropwise with stirring while maintaining the reaction temperature below 8° C. After warming to ambient temperature the organic layer is separated, washed with aqueous sodium bicarbonate, dried over sodium sulfate and evaporated without heat to yield 7.27 g. of 4-ethoxy-3-thiophenecarbonyl azide.

A 48 ml. portion of 97% formic acid is heated to boiling under argon and 18.4 g. of 4-ethoxy-3-thiophenecarbonyl azide is added in portions to the refluxing acid. Excess formic acid is removed, the mixture is cooled, water is added and the mixture is filtered giving N-(4-ethoxy-3-thienyl)-formamide, as a dark pink solid.

A mixture of 15.4 g. of N-(4-ethoxy-3-thienyl)formamide in 50 ml. of 2 N ethanolic hydrogen chloride and 90 ml. of ethanol is refluxed on a steam bath for 2 hours, filtered and evaporated to a residue. Water is added to the residue, which is cooled, made alkaline with 5 N sodium hydroxide and extracted with dichloromethane. The extracts are dried over magnesium dulfate, filtered and evaporated giving 3-amino-4-ethoxythiophene as a dark amber oil.

A mixture of 14.4 g. of isatoic anhydride, 22 ml. of dimethylsulfoxide and some ground glass is stirred and put in an oil bath at 120° C. A mixture of 12.6 g. of 3-amino-4-ethoxythiophene in 17 ml. of dimethylsulfoxide is added dropwise over 30 minutes at 120°–129° C. The mixture is heated at 125°–129° C. for one hour, cooled, poured into ice and water and extracted with dichloromethane. The extract is dried over magnesium sulfate, filtered and evaporated to an oil. This oil is dissolved in methanol, filtered, cooled and a few drops of water are added. The solid is removed by filtration and the filtrate is evaporated to an oil. This oil is dissolved in methanol, a few drops of water are added and the mixture is chilled overnight. The solid is collected by filtration giving o-amino-N-(4-ethoxy-3-thienyl)-benzamide.

A 7.2 g. portion of the above benzamide in 100 g. of polyphosphoric acid is heated at 115°–125° C. for 2 hours, cooled, poured into ice and water and extracted with chloroform. The extract is washed with water, dried over magnesium sulfate, filtered and evaporated, giving 4H-thieno[3,4-b][1,4]benzodiazepin-9(10H)-one as a yellow solid.

To a mixture of 15.0 g. of N-methylpiperazine, 6.3 g. of titanium tetrachloride and 7 ml. of anisole in 67 ml. of toluene is added a mixture of 7.6 g. of N-methylpiperazine and 7.1 g. of 4H-thieno[3,4-b][1,4]benzodiazepin-9(10H)-one in 7 ml. of toluene. This mixture is stirred and refluxed for 2 hours, cooled and 11 ml. of 2-propanol, 5 g. of diatomaceous earth and 10.2 ml. of ammonium hydroxide are added. The mixture is filtered and the solid washed with toluene. The toluene filtrate and washings are washed with water, the toluene layer is separated and extracted with three 150 ml. portions of 3 N hydrochloric acid. The acidic extracts are combined, cooled, made alkaline with ammonium hydroxide and extracted with dichloromethane. This extract is dried, filtered, evaporated to 75 ml. and filtered through magnesium silicate. This filtrate is evaporated giving 9-(4-methyl-1-piperazinyl)-4H-thieno[3,4-b][1,4]benzodiazepine.

A solution of 1.8 g. portion of 9-(4-methyl-1-piperazinyl)-4H-thieno[3,4-b][1,4]benzodiazepine in 21 ml. of 97% formic acid is cooled in an ice bath and 2.1 g. of sodium borohydride pellets are added portionwise over a 30 minute period. The mixture is stirred for 2 hours, cooled, water is added, the mixture is made alkaline with ammonium hydroxide and extracted with chloroform. The extract is dried over magnesium sulfate, filtered and evaporated. The residue is dissolved in 15 ml. of warm ethanol, filtered and 0.7 g. of fumaric acid in 10 ml. of ethanol is added giving the desired compound as the fumarate salt, m.p. 206°–208° C. (dec.).

EXAMPLE 2

9-(4-Methyl-1-piperazinyl)-4H-thieno-[3,4-b][1,4]benzodiazepine fumarate

A 1.8 g. portion of 9-(4-methyl-1-piperazinyl)-4H-thieno[3,4-b][1,4]benzodiazepine is dissolved in 20 ml. of ethanol and filtered. To the filtrate is added a solution of 0.7 g. of fumaric acid in 10 ml. of ethanol. The resulting solid is recovered by filtration and dried, giving the desired product as the fumarate salt, m.p. 232°-233° C. (dec.).

EXAMPLE 3

7-Chloro-9-(4-methyl-1-piperazinyl)-4H-thieno[3,4-b][1,4]benzodiazepine

A 2.13 g. portion of 5-chloroisatoic anhydride, 37 ml. of dimethylsulfoxide and some ground glass are heated in an oil bath at 125° C. A 15.4 g. portion of 3-amino-4-ethoxythiophene in 30 ml. of dimethylsulfoxide is added dropwise over a 1.5 hour period. The mixture is stirred at 125° C. for 1.5 hours and then at room temperature overnight, poured into ice and water and extracted twice with dichloromethane and twice with chloroform. The extracts are dried over magnesium sulfate, filtered and evaporated to an oily residue. This residue is dissolved in ether, filtered and hydrogen chloride is bubbled through the filtrate, giving a solid which is recrystallized from ethanol-ether giving 18.9 g. of 2-amino-5-chloro-N-(4-ethoxy-3-thienyl)benzamide hydrochloride. An aqueous solution of a 17.9 g. portion of 2-amino-5-chloro-N-(4-ethoxy-3-thienyl)benzamide hydrochloride is converted to the base compound by basifying with 5 N sodium hydroxide.

A 2.96 g. portion of the above base in 30 g. of polyphosphoric acid is heated at 120°-123° C. for 30 minutes. The mixture is cooled, poured into ice and water, filtered, washed with water, sodium bicarbonate solution and dried giving 2.2 g. of 7-chloro-4H-thieno[3,4-b][1,4]benzodiazepin-9(10H)-one.

To a solution of 7 ml. of anisole, 3.8 ml. of titanium tetrachloride and 1.5 g. of methylpiperazine in 67 ml. of toluene is added a mixture of 6.7 g. of 7-chloro-4H-thieno-[3,4-b][1,4]benzodiazepin-9(10H)-one and 7.6 g. of methylpiperazine in 7 ml. of toluene. The mixture is refluxed with stirring overnight, cooled and 10 ml. of isopropyl alcohol, 5 g. of diatomaceous earth and 10 ml. of ammonium hydroxide are added. The mixture is filtered and washed with toluene. The toluene is washed with water and then extracted with three 150 ml. portions of 3 N hydrochloric acid. The acid extracts are made alkaline with ammonium hydroxide and extracted with dichloromethane. This extract is dried over magnesium sulfate, filtered and the solvent is evaporated. The residue is crystallized from dichloromethane-hexane giving the desired product, m.p. 191°-194° C.

EXAMPLE 4

7-Chloro-4-methyl-9-(4-methyl-1-piperazinyl)-4H-thieno[3,4-b][1,4]benzodiazepine fumarate A mixture of 1.8 g. of 7-chloro-9-(4-methyl-1-piperazinyl)-4H-thieno[3,4-b][1,4]benzodiazepine in 20 ml. of 95-97% formic acid is stirred and cooled. A 2 g. portion of sodium borohydride pellets is added over 30 minutes. The mixture is stirred for several hours with the incremental addition of more sodium borohydride until thin layer chromatography shows that no more starting material remains. The mixture is cooled, water is added and the mixture is made alkaline with ammonium hydroxide. The mixture is extracted with dichloromethane, the extracts are dried over magnesium sulfate and evaporated. The residue is dissolved in dichloromethane and filtered through magnesium silicate giving a glass. This glass is dissolved in 20 ml. of ethanol and a solution of 0.34 g. of fumaric acid in 4 ml. of ethanol is added. The solid is recrystallized from ethanol, giving the desired product, m.p. 222°-224° C. (dec.).

EXAMPLE 5

7-Fluoro-9-(4-methyl-1-piperazinyl)-4H-thieno[3,4-b][1,4]benzodiazepine

A 13.9 g. portion of 6-fluoroisatoic anhydride, 20 ml. of dimethylsulfoxide and some ground glass are heated in an oil bath at 125° C. and stirred while adding dropwise a solution of 11.0 g. of 3-amino-4-ethoxythiophene in 25 ml. of dimethylsulfoxide over a period of 2 hours. The mixture is cooled, poured into ice and water and extracted several times with chloroform. The extracts are dried over magnesium sulfate, filtered and evaporated. The oily residue is dissolved in ether, filtered through magnesium silicate and evaporated. The residue is dissolved in dichloromethane, filtered through magnesium silicate and evaporated. This residue is dissolved in ether, filtered and hydrogen chloride gas is bubbled through the filtrate. The grey solid is collected, added to 500 ml. of water and treated with 1 N sodium hydroxide giving 2-amino-N-(4-ethoxy-3-thienyl)-5-fluorobenzamide.

A 5.7 g. portion of 2-amino-N-(4-ethoxy-3-thienyl)-5-fluorobenzamide and 60 g. of polyphosphoric acid are stirred and heated at 120°-128° C. for one hour, cooled and poured into ice and water. The solid is recovered by filtration, washed with water, sodium carbonate solution, sodium bicarbonate solution and then water and dried at 60° C. overnight, giving 7-fluoro-4H-thieno[3,4-b][1,4]benzodiazepin-9(10H)-one.

To a stirred mixture of 14.0 g. of N-methylpiperazine, 3.4 ml. of titanium tetrachloride and 6 ml. of anisole in 60 ml. of toluene is added a mixture of 6.7 g. of N-methylpiperazine and 5.6 g. of 7-fluoro-4H-thieno[3,4-b][1,4]benzodiazepin-9(10H)-one in 6 ml. of toluene. The mixture is treated as described in Example 1, giving the desired product as a tan solid, m.p. 224°-227° C. (dec.).

EXAMPLE 6

7-Fluoro-4-methyl-9-(4-methyl-1-piperazinyl)-4H-thieno[3,4-b][1,4]benzodiazepine hemifumarate A mixture of 3.1 g. of 7-fluoro-9-(4-methyl-1-piperazinyl)-4H-thieno[3,4-b][1,4]benzodiazepine and 34.5 ml. of 97% formic acid is stirred and cooled while 3.8 g. of sodium borohydride pellets are added over a 30 minute period. The procedure of Example 4 is followed producing the base compound which is treated with fumaric acid in ethanol to give the desired fumarate salt as a tan solid, m.p. 189°-195° C. (dec.).

EXAMPLE 7

9-(1-Piperazinyl)-4H-thieno[3,4-b][1,4]benzodiazepine fumarate

To a mixture of 7 ml. of anisole, 3.8 ml. of titanium tetrachloride and 12.9 g. of piperazine in 67 ml. of toluene is added a mixture of 7.1 g. of 4H-thieno[3,4-b][1,4benzodiazepin-9(10H)-one and 6.5 g. of piperazine in 7 ml. of toluene. This mixture is stirred and refluxed for 3 hours, cooled and 11 ml. of isopropanol, 5 g. of celite and 10.2 ml. of ammonium hydroxide are added and the procedure of Example 3 is followed giving the base compound as a tan solid.

A 0.57 g. portion of this base in 20 ml. of ethanol is converted to the desired fumarate salt, a tan solid, m.p. 207°-208° C. (dec.).

We claim:

1. A compound selected from the group consisting of those of the formula:

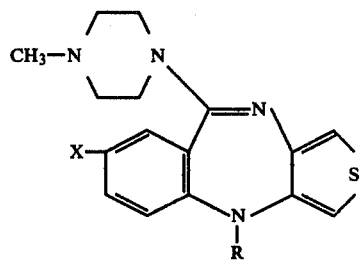

wherein X is hydrogen, fluoro or chloro and R is hydrogen or methyl; and the pharmacologically acceptable acid-addition salts thereof.

2. The compound according to claim 1 wherein X is hydrogen and R is hydrogen.

3. The compound according to claim 1 wherein X is hydrogen and R is methyl.

4. The compound according to claim 1 wherein X is fluoro and R is hydrogen.

5. The compound according to claim 1 wherein X is fluoro and R is methyl.

6. The compound according to claim 1 wherein X is chloro and R is hydrogen.

7. The compound according to claim 1 wherein X is chloro and R is methyl.

* * * * *